(12) United States Patent
Mercati et al.

(10) Patent No.: US 11,839,638 B2
(45) Date of Patent: Dec. 12, 2023

(54) COMPOSITIONS COMPRISING EXTRACT OF POPLAR BUDS AND USES THEREOF

(71) Applicant: Aboca S.p.A. Società Agricola, Sansepolcro (IT)

(72) Inventors: Valentino Mercati, Sansepolcro (IT); Luisa Mattoli, Sansepolcro (IT); Anna Maidecchi, Sansepolcro (IT); Andrea Lugli, Sansepolcro (IT)

(73) Assignee: Aboca S.p.A. Società Agricola, Sansepolcro (IT)

( * ) Notice: Subject to any disclaimer, the term of this patent is extended or adjusted under 35 U.S.C. 154(b) by 243 days.

(21) Appl. No.: 16/303,474

(22) PCT Filed: May 22, 2017

(86) PCT No.: PCT/IB2017/053000
§ 371 (c)(1),
(2) Date: Nov. 20, 2018

(87) PCT Pub. No.: WO2017/203414
PCT Pub. Date: Nov. 30, 2017

(65) Prior Publication Data
US 2020/0101127 A1 Apr. 2, 2020

(30) Foreign Application Priority Data
May 24, 2016 (IT) .................. 102016000053369

(51) Int. Cl.
*A61K 36/76* (2006.01)
*A61K 9/19* (2006.01)
*A61K 47/10* (2017.01)
*A61K 47/36* (2006.01)

(52) U.S. Cl.
CPC .............. *A61K 36/76* (2013.01); *A61K 9/19* (2013.01); *A61K 47/10* (2013.01); *A61K 47/36* (2013.01); *A61K 2236/333* (2013.01)

(58) Field of Classification Search
CPC .................................................. A61K 36/00
USPC ...................................................... 424/725
See application file for complete search history.

(56) References Cited

FOREIGN PATENT DOCUMENTS

| CA | 2908185 | * | 9/2014 |
|---|---|---|---|
| CN | 1666753 | * | 9/2005 |
| CN | 103315191 | * | 9/2013 |
| JP | 2012062321 | * | 3/2012 |
| RU | 2135201 | * | 8/1999 |
| WO | WO-0067767 A1 | | 11/2000 |
| WO | WO-2015059683 A1 | | 3/2015 |
| WO | WO-2017203414 A1 | | 11/2017 |

OTHER PUBLICATIONS

Virey, Trattato compiuto di farmacia teorica o pratica, 1836, vol. 2, fourth ed,, pp. 43-46.*
Mother earth living, 2 pages, 2011.*
Anonymous, "Hand Cream", Jul. 1, 2008 (Jul. 1, 2008), Retrieved from the Internet: URL:http://www.gnpd.com/sinatra/recordpage/941356/from_search/8QxEqAIyKw/?page=1 [retrieved on Jan. 11, 2017].
Anonymous, "Honey Lemon Throat Lozenges", Feb. 1, 2015 (Feb. 1, 2015), Retrieved from the Internet: URL:http://www.gnpd.com/sinatra/recordpage/3006879/from_search/LZdtRQ83S4/?page=1 [retrieved on Jan. 11, 2017].
Anonymous, "Propolgemma: Propolis Spray for Adults", Nov. 1, 2016 (Nov. 1, 2016), Retrieved from the Internet: URL:http://www.gnpd.com/sinatra/recordpage/4393677/from_search/waL2IHpAMN/?page=1 [retrieved on Jan. 11, 2017].
Drum, R., et al., "Poplar Buds, Grindelia Buds & Fig Leaves", Mar. 27, 2009 (Mar. 27, 2009), Retrieved from the Internet: URL:https://web.archive.org/web/20090327124300/http://www.ryandrum.com/twobudsoneleaf.htm, [retrieved on Jan. 11, 2017].
Dudonné, S., et al., "Phenolic Composition and Antioxidant Properties of Poplar Bud (*Populus nigra*) Extract: Individual Antioxidant Contribution of Phenolics and Transcriptional Effect on Skin Aging", Journal of Agricultural and Food Chemistry, vol. 59, No. 9, May 11, 2011 (May 11, 2011), p. 4527-4536.
International Search Report and Written Opinion for International Application No. PCT/IB2017/053000, dated Jul. 26, 2017, E.P.O., Netherlands, 11 pages.
Virey, J.J.,"Unguento populeo riformato", "Trattato compiuto di farmacia teorica e pratica (vol. 2)", p. 43-46, Jan. 1, 1836 (Jan. 1, 1836), Verona.
Wang Kai et al, "Anti-inflammatory effects of ethanol extracts of Chinese propolis and buds from poplar (Populuscanadensis)", Journal of Ethnopharmacology, Elsevier Ireland LTD, IE, vol. 155, No. 1, Jun. 2, 2014 (Jun. 2, 2014), p. 300-311.
Zamboni, E., et al., "Unguento al pioppo", Aug. 19, 2015 (Aug. 19, 2015), Retrieved from the Internet: URL:https://web.archive.org/web/20150819110104/http://www.sosrosarno.org/agricoltura-sostenibile/item/download/19_e28111cb95524744926dd202d4f034f8.html [Retrieved on Jan. 11, 2017].

* cited by examiner

*Primary Examiner* — Michael V Meller
(74) *Attorney, Agent, or Firm* — STERNE, KESSLER, GOLDSTEIN & FOX P.L.L.C.

(57) ABSTRACT

The present invention relates to a composition comprising extract of poplar buds for use in the treatment of oropharyngeal cavity, urinary apparatus, digestive/excretory apparatus, skin affections and of bacterial infections.

8 Claims, 12 Drawing Sheets

Figure 1A:
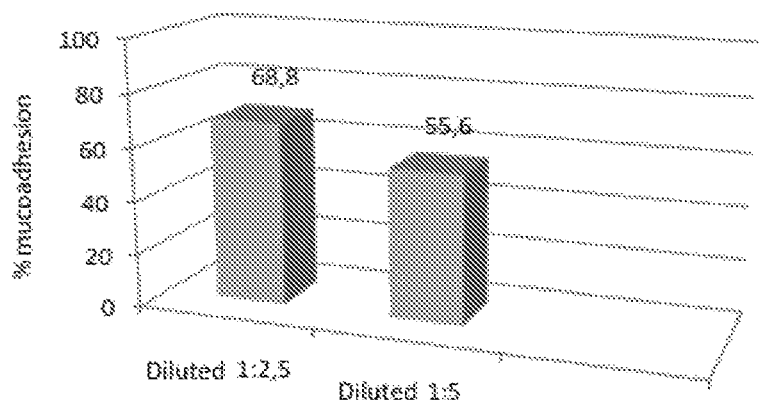

```
ALCOHOLIC MULTI-FRACTION
        EXTRACT
  Fraction 1 (polar fraction)
``` e.   Concentration
     Lyophilisation

```
LYOPHILISED MULTI-FRACTION
         EXTRACT
   Fraction 1 (polar fraction)
```

FIG. 9

COMPOSITIONS COMPRISING EXTRACT OF POPLAR BUDS AND USES THEREOF

The present invention relates to a composition comprising extract of poplar buds for use in the treatment of oropharyngeal cavity, urinary apparatus, digestive/excretory apparatus, skin affections and of bacterial infections.

STATE OF THE PRIOR ART

It is known in the literature that the resinous exudate of black poplar (*Populus nigra*) constitutes the base element of European propolis, and in general of bee-produced propolis in temperate zones.

Propolis, known for its many pharmacological activities is a substance produced by bees following collecting, by the latter, of resinous exudates (mainly of black poplar). On average, it is comprised of 25-35% beeswax, 5% pollen, 5% of various substances present on bee legs and about 50% of plant resins.

Various uses of poplar buds-based drugs are also known in the literature.

Given the constant and increasing interest for the use of substances of natural origin for the treatment of numerous affections, and given the current dramatic extinction hazard to which bees are exposed, it is important to find products of natural origin which may comparably replace in a comparable, or even more effective manner, bee-produced substances.

SUMMARY OF THE INVENTION

The Authors of the present invention have analysed extracts of poplar buds in order to verify the possible use thereof for therapeutic purposes as an alternative completely of plant origin to propolis.

Unlike propolis, the extracts of poplar buds also entail the advantage of not containing substance of animal origin and allergenic substances such as pollens.

The Authors of the present invention have surprisingly verified that, with respect to European propolis, poplar buds extracts exhibit comparable or even greater mucoadhesive properties.

The Authors of the invention have also demonstrated for the first time an effective antibacterial activity, in particular against *Streptococcus pyogenes*, *Pseudomonas aeruginosa* and *Staphylococcus aureus*, of extracts of poplar buds, optionally lyophilised, optionally co-lyophilised with natural gums (gum-supported).

Therefore, object of the present invention is a composition comprising

Extract of poplar buds to a percentage in weight from 0.1 to 70% and one or more of pharmaceutically acceptable carriers, excipients, flavours, preservatives for use in the treatment of oropharyngeal cavity, urinary apparatus, digestive/excretory apparatus, skin affections and of bacterial infections for use in the treatment of oropharyngeal cavity, urinary apparatus, digestive/excretory apparatus, skin affections and of bacterial infections.

Moreover, object of the present invention is the treatment of oropharyngeal cavity, urinary apparatus, digestive/excretory apparatus, skin affections and of bacterial infections by administering the mixture or the composition of the invention to a subject affected by said disorders.

DETAILED DESCRIPTION OF THE FIGURES

FIG. 1, Mucoadhesion assay of various formulations, carried out as described in Example 1.

Figure 1B:
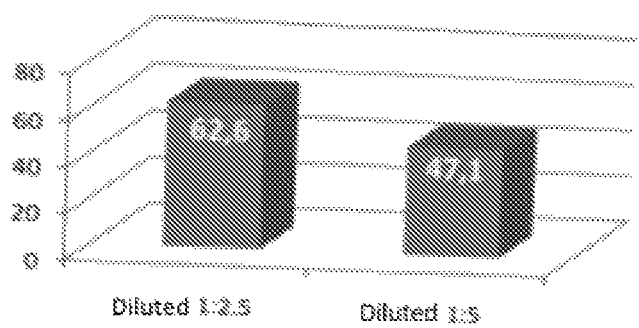
Figure 1C:
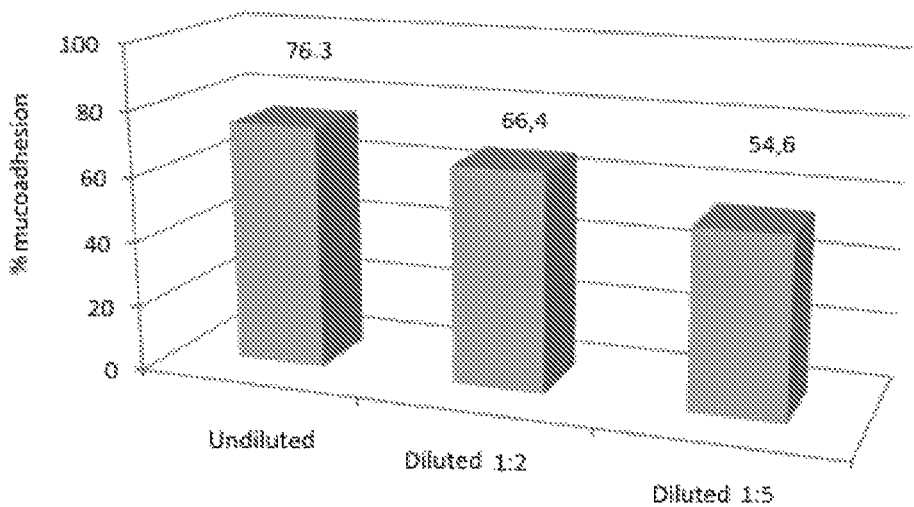
Figure 1D:
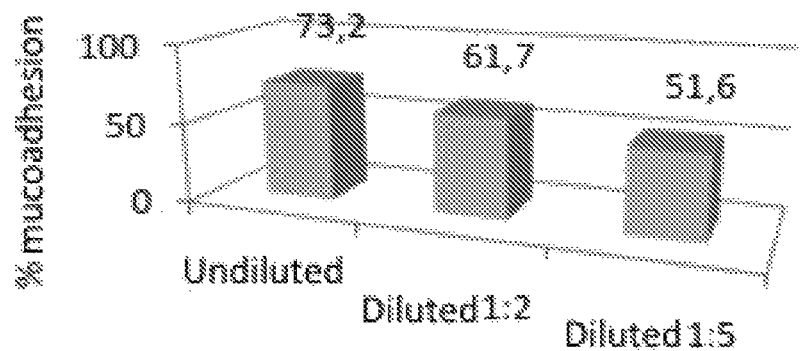

FIG. 1A: Mucoadhesivity percentage of the composition—diluted (1:2.5 and 1:5) Example solid composition 4 towards human buccal cells; FIG. 1B: Mucoadhesivity percentage of the composition—diluted (1:2.5 and 1:5) Example solid composition 3 towards human buccal cells; FIG. 1C: Mucoadhesivity percentage of the composition—non-diluted or diluted (1:2 and 1:5) Example fluid composition 4 towards human buccal cells; FIG. 1D: Mucoadhesivity percentage of the composition—non-diluted or diluted (1:2 and 1:5) Example fluid composition 3 towards human buccal cells.

FIG. 2—Resistance of the mucoadhesive layer (obtained with the different formulations of the invention at various dilutions and in different times) at different times to a simulated salivary solution (0.9% NaCl physiological solution).

Figure 2A:
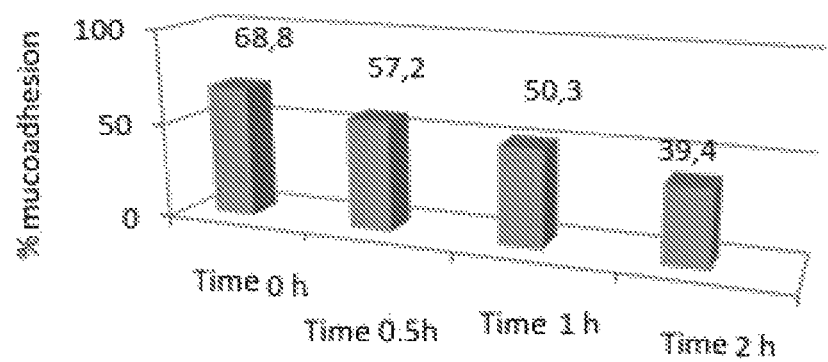
Figure 2B:
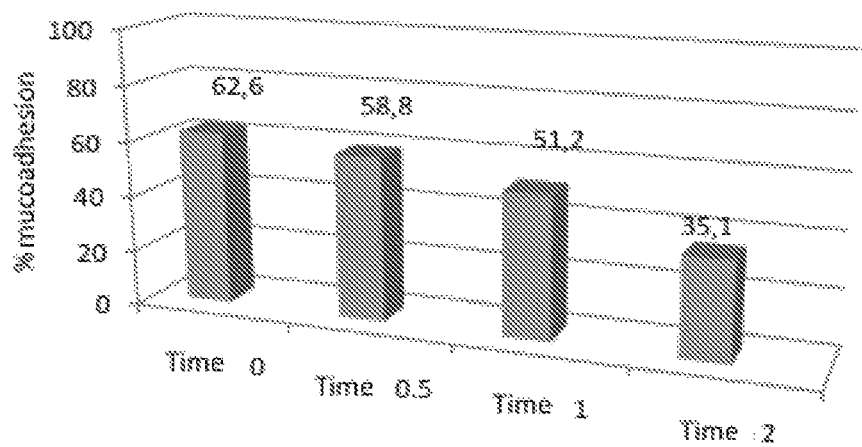
Figure 2C:
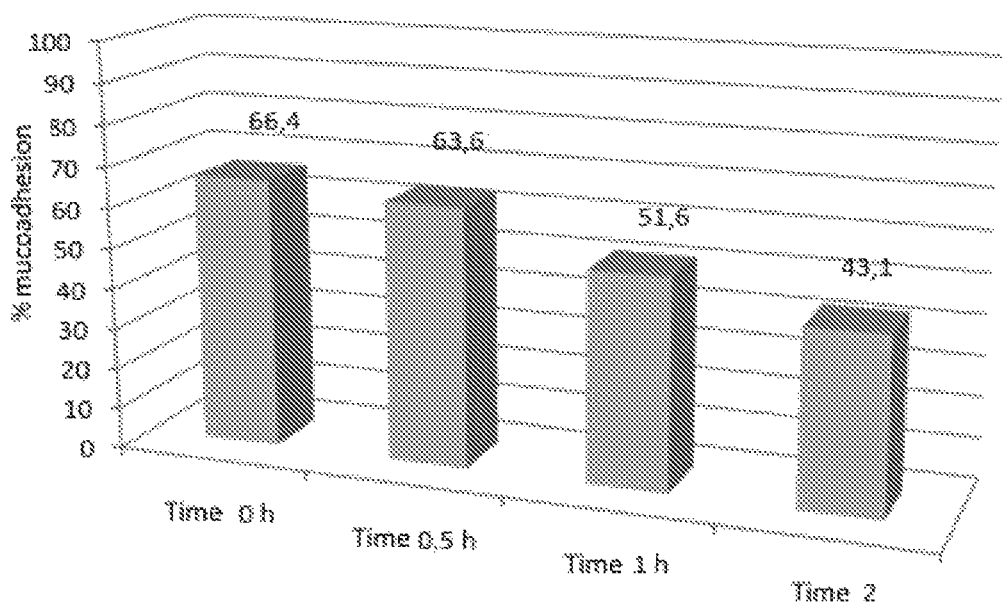

FIG. 2A: composition—(diluted 1:2.5) Example solid composition 4 at different times (0 h, 0.5 h, 1 h and 2 h) to a simulated salivary solution (0.9% NaCl physiological solution); FIG. 2B: composition—(diluted 1:2.5) Example solid composition 3 at different times (Time: 0 h, 0.5 h, 1 h and 2 h) to a simulated salivary solution (0.9% NaCl physiological solution); FIG. 2C: composition—(diluted 1:2) Example fluid composition 4 at different times (Time: 0 h, 0.5 h, 1 h and 2 h) to an artificial salivary solution.

FIG. 3: IL6 production in barrier assay; graphs show the protection exerted by the composition of the invention on the cells, and data are expressed in terms of fold over (F.O.) compared to the control C−

Fold Over C−=[measured IL-6]/[C−IL-6]

Figure 3A:
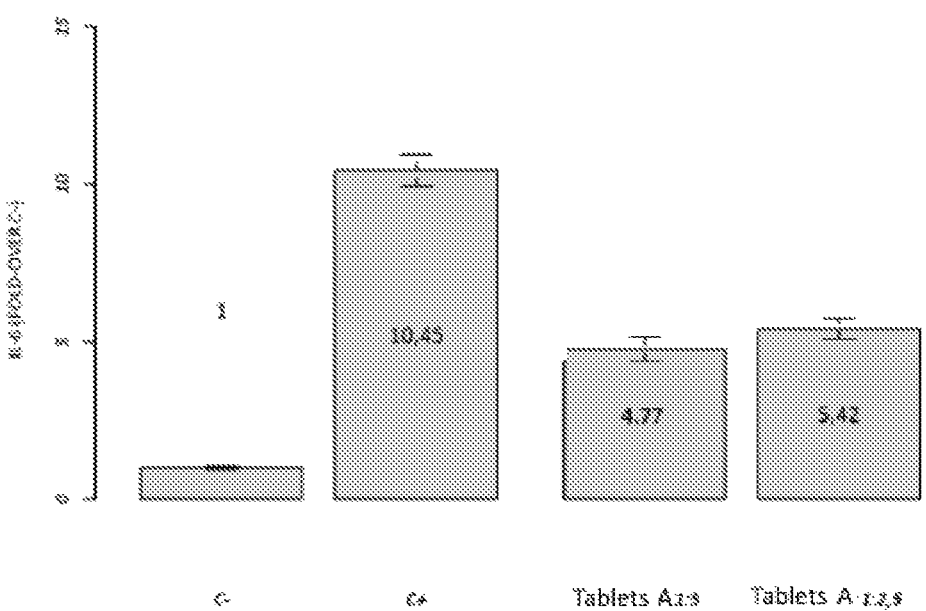
Figure 3B:
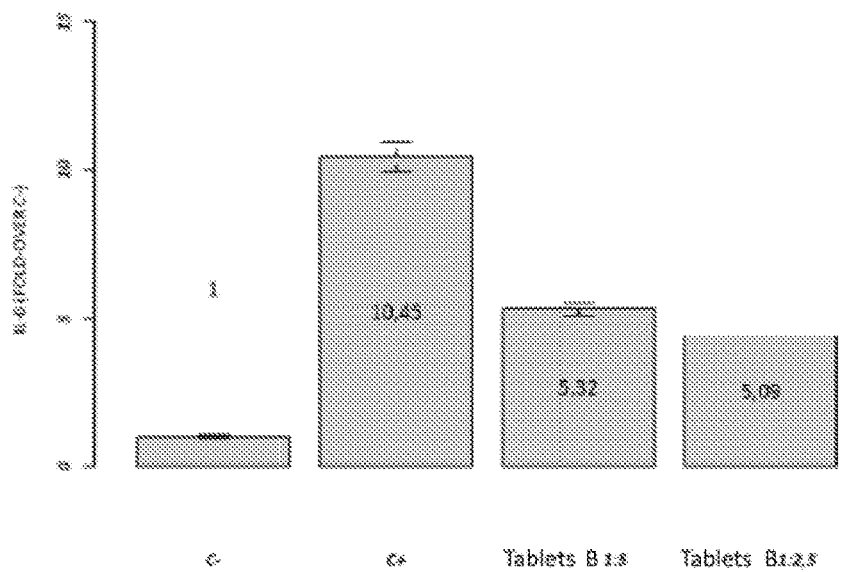
Figure 3C:
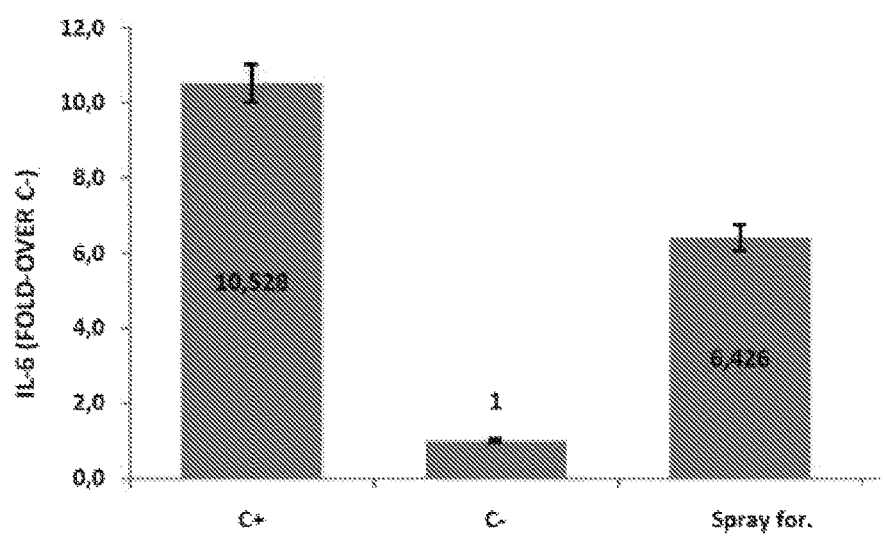
Figure 3D:
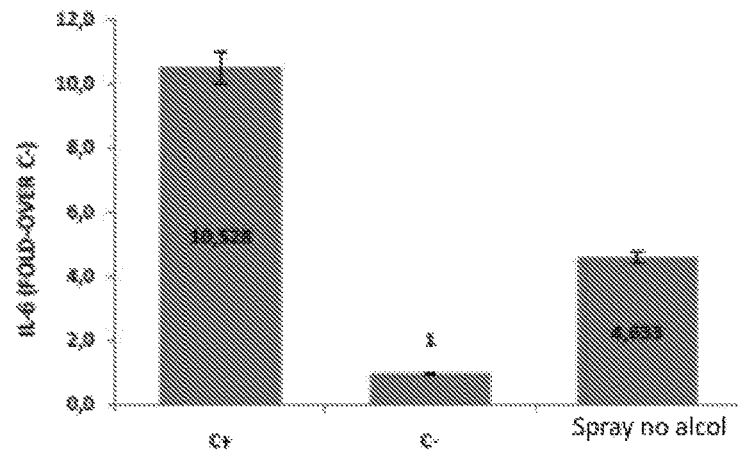

FIG. 3A: composition—Example solid composition 4, FIG. 3B: composition—Example solid composition 3, FIG. 3C: composition—Example fluid composition 4, FIG. 3D: composition—Example fluid composition 3.

FIG. 4 graphically depicts the barrier effect calculated for the various embodiments of the invention described, in term of percentage of IL6 release inhibition.

Figure 4A:
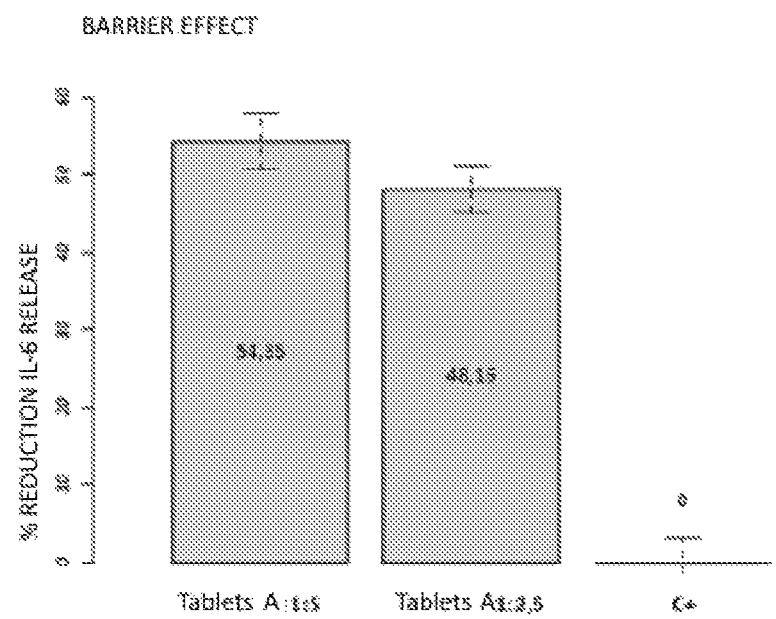
Figure 4B:
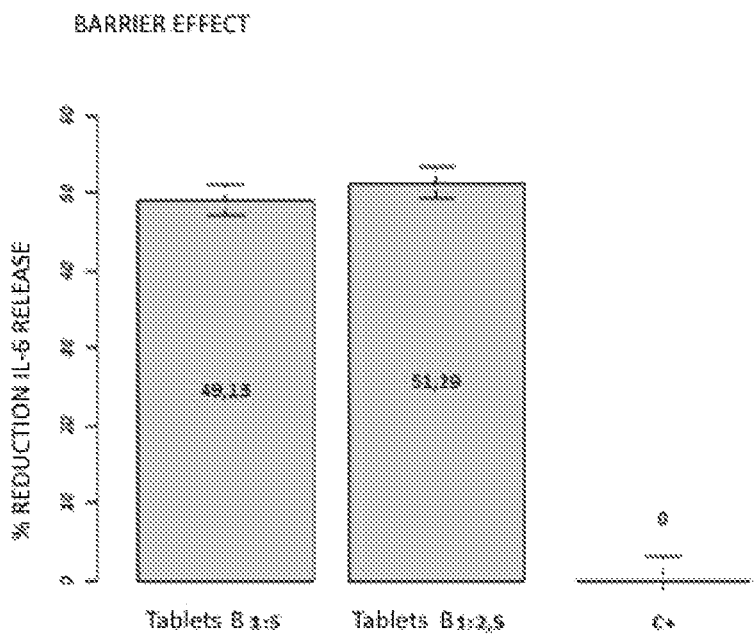
Figure 4C:
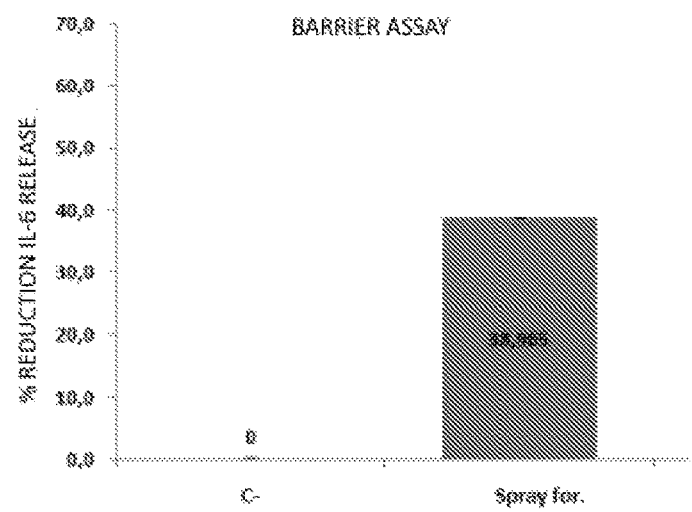
Figure 4D:
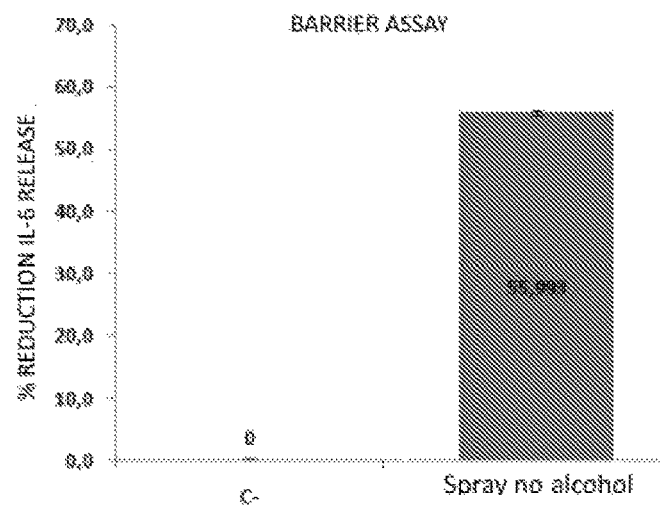

FIG. 4A: composition—Example solid composition 4, FIG. 4B: composition—Example solid composition 3, FIG. 4C: composition—Example fluid composition 4, FIG. 4D: composition—Example fluid composition 3.

FIG. 5 graphically depicts cell-produced IL-6 values in term of Fold Over C− in the internal control.

Figure 5A:
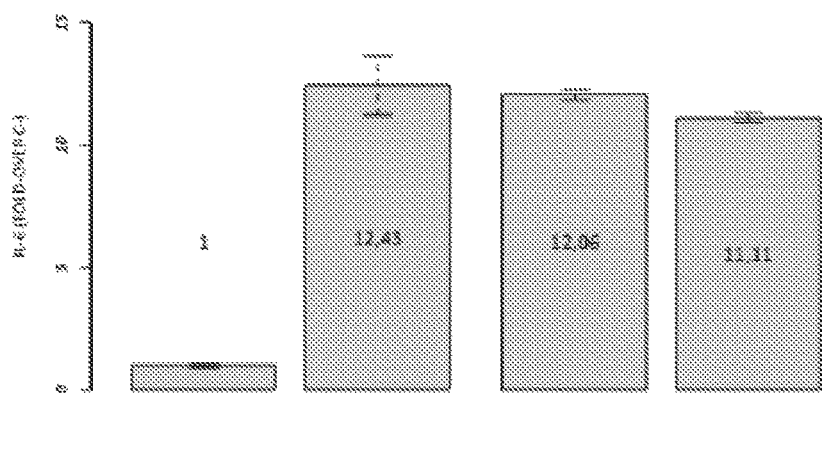
Figure 5B:
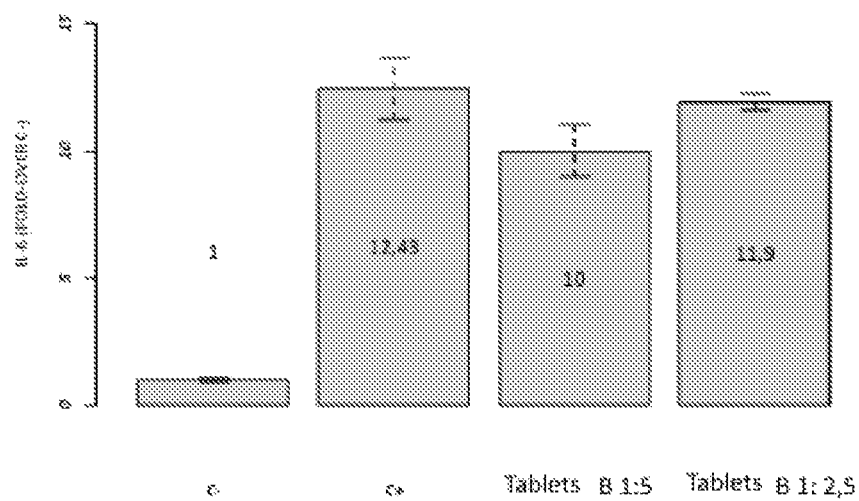
Figure 5C:
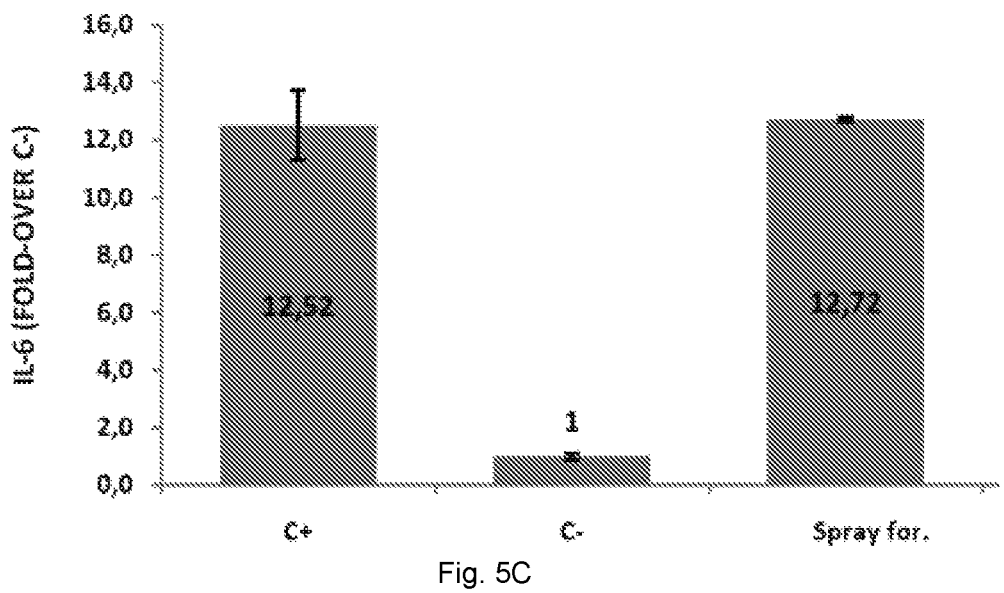
Figure 5D:
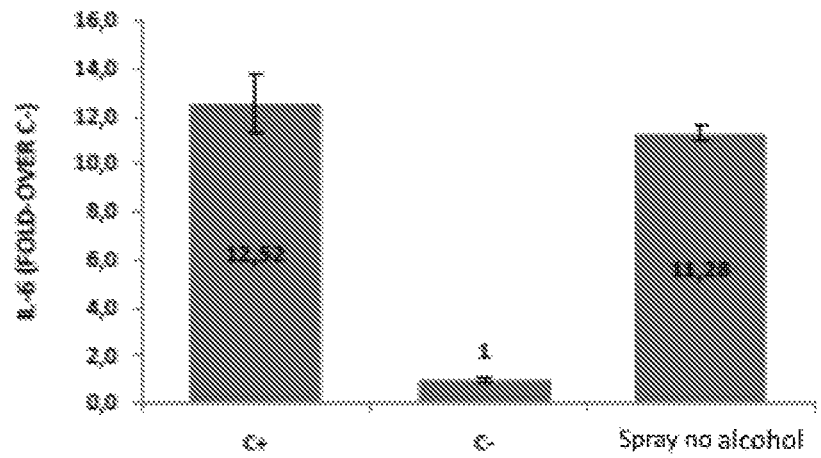

FIG. 5A: composition—Example solid composition 4, FIG. 5B: composition—Example solid composition 3, FIG. 5C: composition—Example fluid composition 4, FIG. 5D: composition—Example fluid composition 3.

Figure 6:
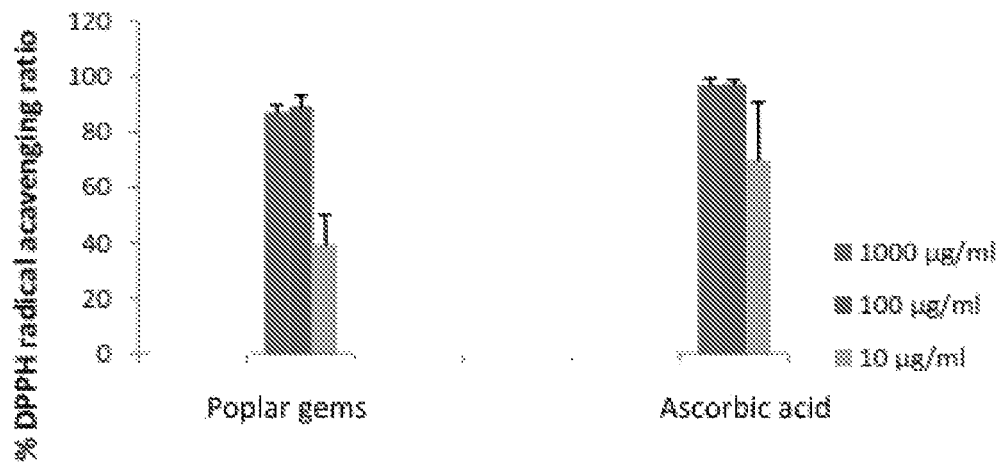

FIG. 6: anti-oxidising activity of the extract of poplar buds according to the invention compared to ascorbic acid.

Figure 7:
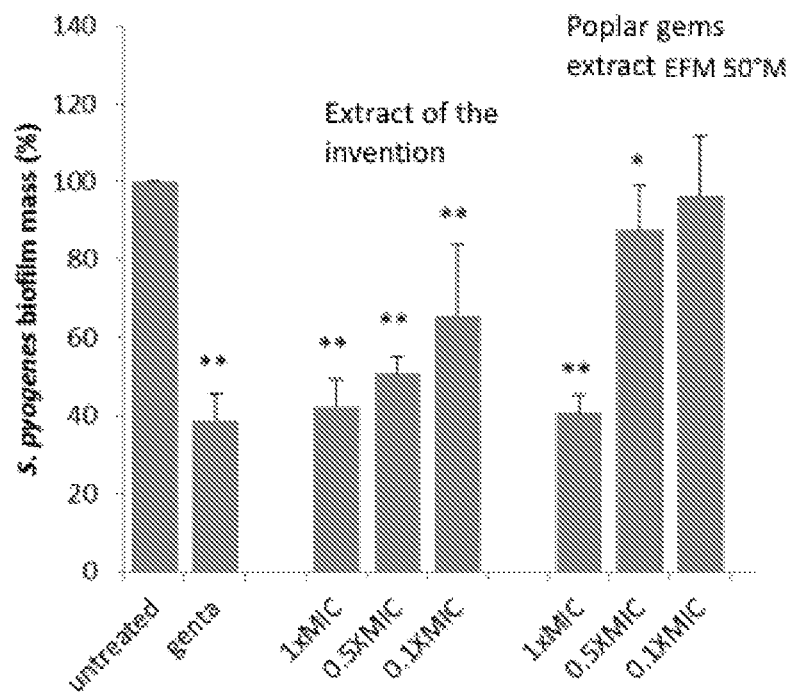

FIG. 7 inhibition activity from bacterial biofilm of the extract of poplar buds according to the invention.

Figure 8:
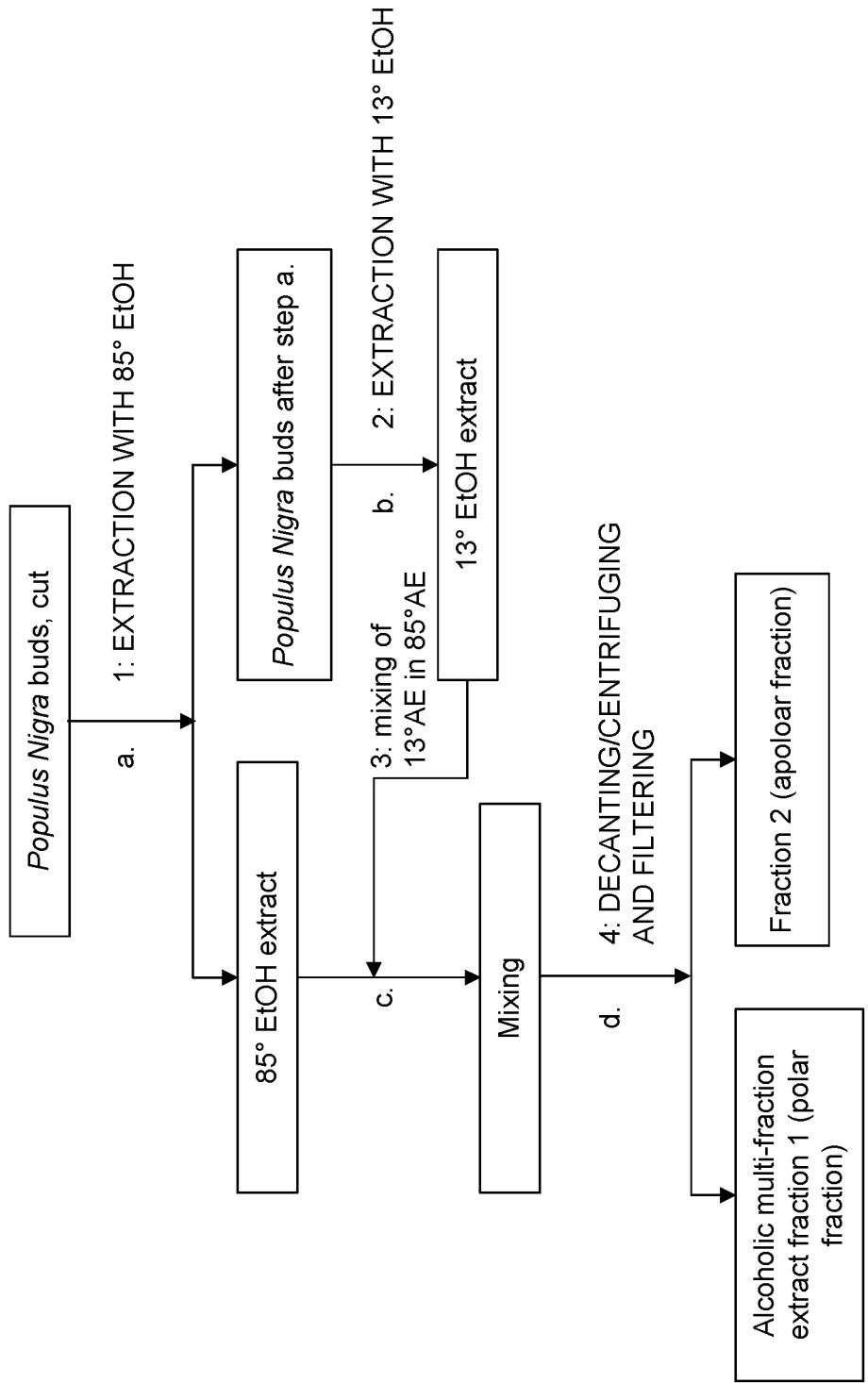

FIG. 8 block diagram of the alcoholic multi-fraction extract of poplar buds.

FIG. 9 block diagram of the lyophilised multi-fraction extract of poplar buds.

Figure 10:
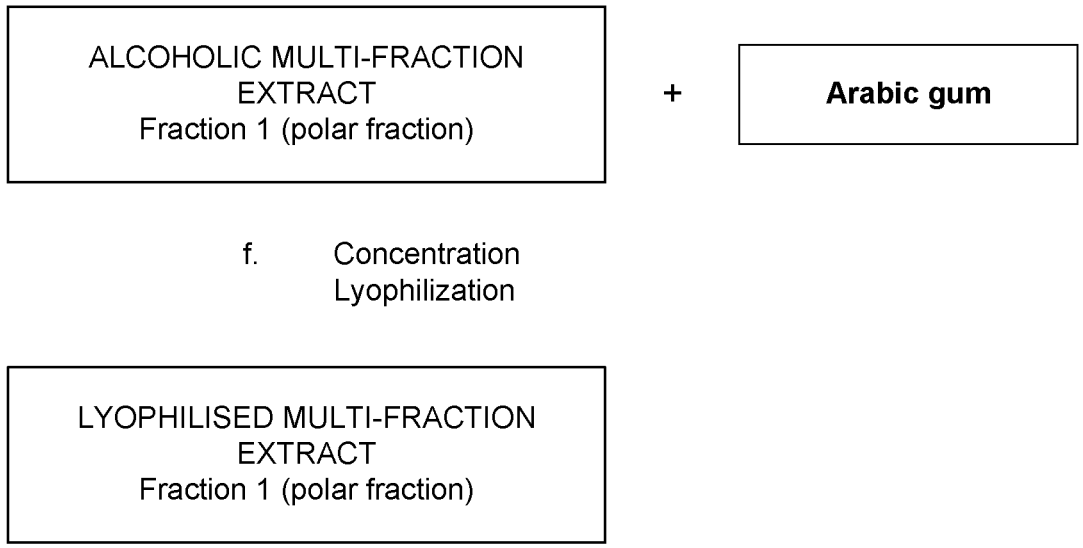

FIG. 10 block diagram of the lyophilised multi-fraction extract supported on arabic gum (or one or more natural gums as indicated below) of poplar buds.

Figure 11:
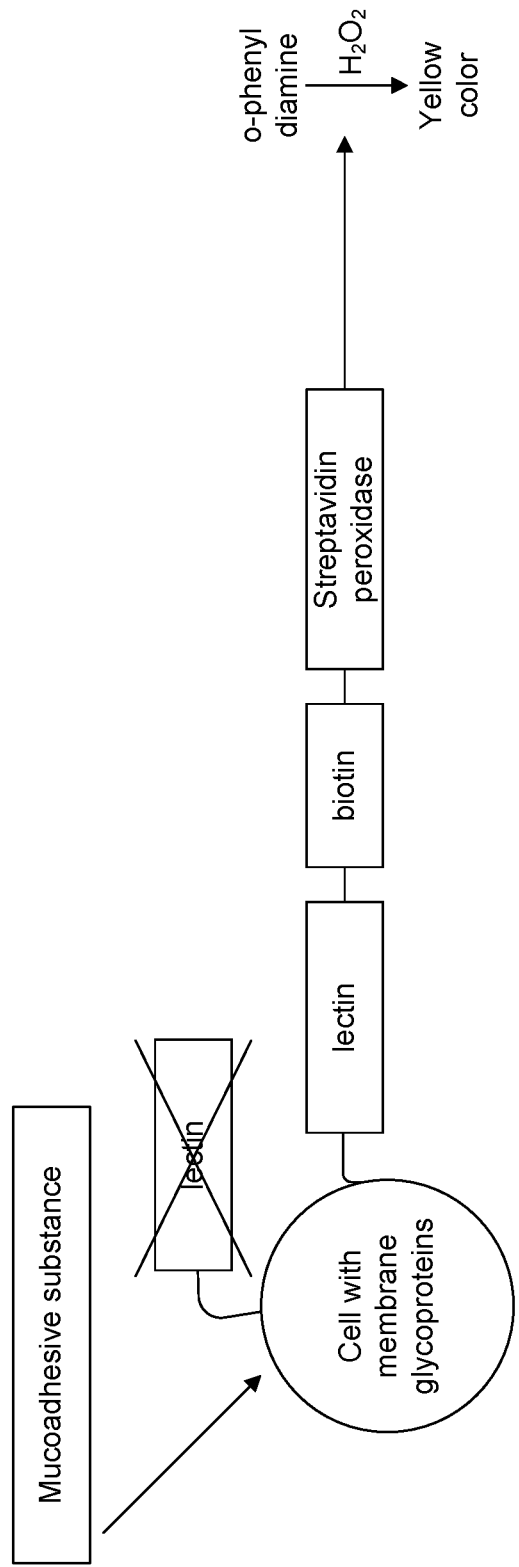

FIG. 11 lectin labelling system.

DETAILED DESCRIPTION OF THE INVENTION

Therefore, object of the present invention is a composition comprising

Extract of poplar buds to a percentage in weight from 0.1 al 70% and one or more of pharmaceutically acceptable carriers, excipients, flavours, preservatives for use in the treatment of oropharyngeal cavity, urinary apparatus, digestive/excretory apparatus, skin affections and of bacterial infections for use in the treatment of oropharyngeal cavity, urinary apparatus, digestive/excretory apparatus, skin affections and of bacterial infections.

According to one embodiment, the composition could comprise or be consisting of:

Extract of poplar buds to a percentage in weight from 0.1 to 70%,

Excipients at a percentage in weight from 1 to 80%

Solvents at a percentage in weight from 0 to 80%

Natural or lyophilised fruit juices at a percentage in weight from 0 to 50%

Natural or artificial flavours at a percentage in weight from 0.05 to 2%

Essential oils at a percentage in weight from 0.01 to 1%.

According to a further embodiment, the composition of the invention could comprise or be consisting of Lyophilised dry poplar buds extract at a percentage in weight from 0.5 to 10%, Excipients at a percentage in weight from 10-97%

Natural or artificial flavours at a percentage in weight from 0.5 to 3%

Essential oils at a percentage in weight from 0.05 to 1%

Powdered or lyophilised fruit juices and/or natural extracts at a percentage in weight from 0.5 to 15%

Sweeteners at a percentage in weight from 1 to 10%.

By "extract of poplar buds", for the purposes of the present invention, it is meant an extract prepared from leaf buds, or mainly leaf buds, of black poplar (*Populus nigra*). In particular, the extract according to the invention is an extract of unopened leaf buds. Buds are found unopened mainly in springtime, which in Europe is usually from March to May.

According to one embodiment of the invention, the sole active principle of the composition is represented by the extract of poplar buds.

In the composition according to any one of the above-reported embodiments, the extract of poplar buds may be associated with a natural gum in an extract:gum ratio comprised in the range of from 1:2-1-20

The composition, as defined above and as further exemplified in the examples below, can be used, as mentioned hereto, for the treatment of oropharyngeal cavity affections. Such affections can be selected, e.g., from sore throat, pharyngitis, aphta, oral cavity inflammation or infection.

In the embodiment wherein said composition is used for the treatment of digestive/excretory apparatus affections, these may be selected from gastritis, reflux, inflammatory bowel diseases, irritable bowel syndrome, hemorrhoids, infections.

Furthermore, the composition of the invention could be used for the treatment of affections of urinary pathways, such as, e.g., cystitis.

In one preferred embodiment, the composition of the invention could be used for the treatment of bacterial infections, among these, the infections of at least one among *Streptococcus pyogenes, Pseudomonas aeruginosa, Staphylococcus aureus* are particularly preferred.

In the treatment of *Streptococcus pyogenes* infections, the composition according to the present invention could be, e.g., used in the treatment of Pharyngitis, Scarlet fever, Pyoderma or impetigo, Erysipelas, Cellulitis, Necrotizing fasciitis, Streptococcal toxic shock syndrome, Bacteraemia, Acute rheumatic fever, Acute glomerulonephritis, Erythema nodosum, P.A.N.D.A.S (Paediatric Autoimmune Neuropsychiatric Disorders Associated with Streptococcal infections), Chronic fatigue syndrome (CFS) and fibromyalgia, Benign Fasciculation Syndrome (BFS).

For the carrying out of the composition of the invention, a hydro-alcoholic extract of poplar buds could preferably be used with a gradation of from 35 to 70 alcohol grades. In a particularly preferred embodiment, the extract could be lyophilised. Optionally, the extract could be co-lyophilised with natural gum in order to increase extract solubility in water and to make the dry extract more easily processable.

However, the data obtained, and that can be seen in the experimental section, show that co-lyophilisation (support) with natural gum increases the mucoadhesive and protective characteristics of the extract, making particularly effective the compositions of the invention comprising the gum-supported extract.

In particular, the extract of poplar buds could be an extract obtainable by a process comprising the following steps:

a. preparing a hydro-alcoholic extract of poplar buds by extraction with 85° ethanol b. preparing a hydro-alcoholic extract of poplar buds by extraction with 13° ethanol c. obtaining a multi-fraction alcoholic extract, by mixing the extracts prepared in a. e b.

d. decanting and/or centrifuging and filtering said alcoholic extract (c.) collecting the supernatant e. the filtered supernatant obtained in d. is subjected to concentration and lyophilisation and, optionally, f. the filtered supernatant obtained in d. is additioned with a natural gum, (selected from gums indicated below in the description or their combinations, in particular additioned with arabic gum) and is therefore subjected to concentration and lyophilisation.

In particular, the extracts in a. and b. can be prepared both by extraction by percolate digestion with motion of the sole extraction solvent, and by extraction with an extractor provided with bladed stirrer, and moving both the solvent and the buds. Extraction can be carried out at a temperature comprised between 35 and 55° C., e.g. at a temperature comprised in the range of 40° C.-50° C. (extremes included), in particular at a temperature of about 40° C. or 50° C.

The extraction can be carried out for a time length of from 4 to 12 hours, e.g. for about 8 hours.

The extracts, prepared in a. and b., are mixed as in point c., preferably in a 50:50 ratio, but may be mixed also in a 35:65, 40:60, 45:55, 55:45, 60:40, 65:35 ratio. The mixing is carried out by gradually adding (addition rate: 15 to 20 l/min) the 13° alcoholic extract in the 85° alcoholic extract, but also the reverse addition is possible. The mixing is carried out at a temperature of 20°±5° C.

The multi-fraction extract prepared at point c. is subjected to clarification by decanting on containers provided with a conical bottom for a minimum of 72 hours. Once said hours have elapsed, the extract is spilled and is filtered on a cellulose filter. Such filtering can be carried out, e.g. on a panel filter with a cut-off of from 0.5 to 50 microns (extremes included) in a single step or in plural consecutive steps, such a, e.g., a cut-off of 0.5 microns, 15 microns, or a cut-off of 30 microns or even higher.

At the end of the filtering, the alcoholic gradation is controlled and adjusted to 50°±15° alcoholic grades.

Alternatively to decanting, the extract can be separated by centrifugation on a vertical centrifuge fed at a flow rate of 5 to 20 l/min.

The extract clarified as in d. could be used tel quel as a multi-fraction alcoholic extract.

The extract clarified as in d. is subjected to a concentration and lyophilisation process as in e. to provide a lyophilised extract that can be used for solid formulations.

The extract clarified as in d., additioned with arabic gum or natural gum is subjected to a concentration and lyophilisation as in f. to provide a lyophilised extract supported on arabic gum, that can be used for solid formulations. Arabic gum, or one or more natural gums, are used in an amount such as to yield a percentage of 10-20% on the solid.

The extract as obtained according to the above-described process is characterised by the following composition:

| Alcoholic multi-fraction extract of poplar buds (Measure unit: mg/100 ml) | |
| --- | --- |
| Total resins | 270 |
| Volatile terpenes | 17.2 |
| Total flavonoids | 170.6 |
| Pinocembrin | 73.40 |
| Galangin | 61.4 |
| Tannins | 13.5 |
| Other PHENOLS (total) | 21.9 |
| Organic acids | 83.9 |
| >20 KDa polysaccharides | 64.5 |
| Lignins | 17.9 |
| Salicylates | 28.1 |
| Minerals | 153 |

The values are given by the mean of analyses of different extracts according to the above-reported methodology.

According to one embodiment, the extract of poplar buds in any form defined above, could be at a weight percentage of from 0.3 to 45 Wt %.

For instance, the composition in fluid form could be according to the following examples Fluid Composition Example 1

| component | Wt % |
| --- | --- |
| EXTRACT OF POPLAR BUDS | 0.70 |
| XANTHAN GUM | 1.00 |
| WATER | 55.40 |
| PEACH FLAVOUR | 0.40 |
| LEMON FLAVOUR | 0.10 |
| CLEAR LEMON JUICE | 1.40 |
| EDIBLE PLANT GLYCERINE, IN KG | 15.00 |
| ORANGE JUICE | 26.00 |
| TOT | 100.00 |

Fluid Composition Example 2

| component | Wt % |
| --- | --- |
| EXTRACT OF POPLAR BUDS | 1.00 |
| GUAR GUM | 1.00 |
| WATER | 55.10 |
| PEACH FLAVOUR | 0.40 |
| LEMON FLAVOUR | 0.10 |
| CLEAR LEMON JUICE | 1.40 |
| EDIBLE PLANT GLYCERINE, IN KG | 15.00 |
| ORANGE JUICE | 26.00 |
| TOT | 100.00 |

Fluid Composition Example 3 (Strong Spray)

| component | Wt % |
| --- | --- |
| ALCOHOLIC POPLAR BUDS EXTRACT 62.7° | 39.76 |
| DEIONISED WATER | 3.92 |
| PLANT GLYCERINE | 55.70 |
| LEMON LOOSE E.O. | 0.01 |
| SWEET ORANGE LOOSE E.O. | 0.01 |
| CITRUS NATURAL FLAVOUR | 0.60 |
| TOT | 100.00 |

Fluid Composition Example 4 (No Alcohol Spray)

| component | Wt % |
| --- | --- |
| LYOPHILISED POPLAR BUDS EXTRACT | 0.55 |
| ARABIC GUM | 4.95 |
| WATER | 51.30 |
| CHERRY FLAVOUR | 0.20 |
| STRAWBERRY FLAVOUR | 0.60 |
| CLEAR LEMON JUICE | 1.40 |
| EDIBLE PLANT GLYCERINE, IN KG | 35.00 |
| CLEAR APPLE JUICE. CONC 70BIX | 6.00 |
| TOT | 100.00 |

Solid Composition Example 1

| component | Wt % |
| --- | --- |
| Lyophilised poplar buds extract | 5.00 |
| Mannitol | 46.14 |
| Tara gum | 6.56 |
| Inulin | 38.60 |
| Raspberry lyophilised juice | 0.40 |
| Peach lyophilised juice | 2.50 |
| Lemon natural flavour | 0.80 |
| Cherry natural flavour | 1 |
| Mallow lyophilised extract | 0.8 |
| Total | 100.00 |

Solid Composition Example 2

| component | Wt % |
| --- | --- |
| Lyophilised poplar buds extract | 10.00 |
| Sorbitol | 46.14 |
| Guar gum | 1.56 |
| Inulin | 15.00 |
| Lemon lyophilised juice | 0.40 |
| Orange lyophilised juice | 25.00 |
| Lemon natural flavour | 0.80 |
| Raspberry natural flavour | 1.10 |
| Mallow lyophilised extract | 0.8 |
| Total | 100.00 |

Solid Composition Example 3 (Adults Tablets)

| component | Wt % |
|---|---|
| Lyophilised poplar buds extract | 1.08 |
| Brown sugar | 71.5 |
| Arabic gum | 10.82 |
| Honey | 3 |
| Lime (tree) extract | 1.5 |
| Orange lyophilised juice | 10.5 |
| Orange flavour | 1.5 |
| Lemon EO | 0.1 |
| Total | 100 |

Solid Composition Example 4 (Children Tablets))

| component | Wt % |
|---|---|
| Lyophilised poplar buds extract | 1.14 |
| Brown sugar | 83.5 |
| Arabic gum | 6.56 |
| Inulin | 1.6 |
| Strawberry lyophilised juice | 2.4 |
| Elder lyophilised juice | 2 |
| Strawberry natural flavour | 1 |
| Cherry natural flavour | 1 |
| Lime (tree) lyophilised extract | 0.8 |
| Total | 100.00 |

The composition of the invention could be, e.g., in the form of powder, tablet, capsule, hard or soft gelatine, syrup, spray, suspension.

Therefore, one or more among pharmaceutically acceptable carriers, excipients, flavours, preservatives known to a technician in the field could be used.

In a broad sense, when made in a fluid form the composition will comprise as active principle the extract of poplar buds in any embodiment described herein and one or more of excipients, solvents, flavours, preservatives, etc., known to a technician in the field. By way of a non-limiting example, as excipients one or more of natural gums could be used, such as, e.g., arabic gum, xanthan gum, guar gum, tara gum or mixtures thereof; natural and synthetic polyalcohols, such as, e.g., sucrose, mannitol, sorbitol, xylitol or mixtures thereof; cellulose and cellulose derivatives, such as, e.g., hydroxyethyl cellulose, hydroxypropyl cellulose, hydroxypropylmethyl cellulose or mixtures thereof; synthetic polymers, such as, e.g., polyvinylpyrrolidone, polymethacrylates or mixtures thereof; maltodextrins, inulin and/or cyclodextrins As solvents, always by way of a non-limiting example, there could be used ethanol, isopropanol, glycerine, propylene glycol or mixtures thereof.

Natural or lyophilised fruit juices could also be used, like, e.g., apple, pear, orange, lemon, raspberry, blueberry juice or mixtures thereof; natural or artificial flavours, such as, e.g., strawberry, lemon, orange, raspberry, peach, cherry, mixed berries, mandarin orange flavour or mixtures thereof; essential oils (E.O.) such as, e.g., lemon, orange, mint, eucalyptus essential oil or mixtures thereof.

Broadly speaking, when made in a solid form, the composition will comprise as active principle the poplar buds extract in any embodiment described herein and one or more of excipients, solvents, flavours, preservatives, etc. known to a technician in the field. By way of a non-limiting example, there could be used as excipients one or more of sugars, such as, e.g., sucrose, mannitol, sorbitol, xylitol or mixtures thereof; cellulose and cellulose derivatives such as, e.g., microcrystalline cellulose, sodium carboxymethyl cellulose, or mixtures thereof; maltodextrins, cyclodextrins and/or inulin. There could be used one or more of starches and starch derivatives, such as, e.g., rice starch, potato starch, corn starch, pregelatinized starch or mixtures thereof; lubricants such as, e.g., stearic acid, magnesium stearate, glyceryl behenate or mixtures thereof; natural and synthetic flavours such as, e.g., strawberry, lemon, orange, raspberry, peach, cherry, mixed berries flavour or mixtures thereof; essential oils, such as, e.g., lemon, orange, mint, eucalyptus essential oil or mixtures thereof; lyophilised fruit juices such as, e.g., apple, pear, orange, lemon, raspberry, blueberry, strawberry, elder juice or mixtures thereof; powder or lyophilised natural extracts of lime (tree), mallow, aloe, althea or mixtures thereof; sweeteners such as, e.g., honey, sugars, aspartame, cyclamates, acesulfame K, stevia extracts, sucralose or mixtures thereof.

Anywhere in the description and in the claims, the term "comprising" could be replaced by the term "consisting in" or "made of".

The following examples are provided in order to further clarify the invention and not for limitative purposes.

EXAMPLES

1. Mucoadhesion Assay

A good mucoadhesive effect is a requirement of paramount importance so that the product may remain in the intended site of action (pharyngeal mucosa) and mechanically carry out thereat its protective and curative actions, as already explained in the description above. The main aim of this assay is to assess the in vitro adhesion of the composition of the invention in different formulations on a suitable cell model envisaging the use of buccal cells. A second aim of the assay is to determine bioadhesion resistance over time to a flow of artificial salivary solution. Mucoadhesion of the composition of the invention in different formulations was determined by assessment of the product ability to adhere to cells by inhibiting lectin (a protein having a high affinity for glucoside and mannoside residues) bonding with membrane glycoproteins. The extent of mucoadhesion is measured by a colorimetric reaction enabling to quantify the sites on glycoproteins not engaged by the lectin, as engaged by the mucoadhesive product. The colorimetric reaction is possible thanks to a peculiar lectin labelling system.

The decrease in the absorbency value is proportional to the ability of the product to adhere ("mucoadhere") to cells. The mucoadhesive ability is expressed as a percentage of inhibition of glycoprotein/lectin bonding, and represents the percentage of mucosal sites occupied by the product according to the equation:

Percentage of mucoadhesion of the product=(1−abs sample/abs control)×100

The product is applied after dilution, taking into account the fact that in real use, right after delivery, a mixing with the saliva present in the oropharyngeal cavity occurs. The following graphs depict the results obtained with different samples of composition according to the invention in different formulations.

TABLE 1

Percentage of mucoadhesion of the product in the form of orally dissolving tablets according to the example (Example solid composition 3) diluted 1:2.5 towards human buccal cells.

| Samples | Diluted 1:2.5 | Diluted 1:5 |
|---|---|---|
| A | 69.5 | 55.3 |
| B | 71.4 | 58.8 |
| C | 65.6 | 52.7 |
| Mean ± S.D. (%) | 68.8 ± 3.0 | 55.6 ± 1.8 |

Dilution 1:2.5 versus 1:5 $p < 0.01$

TABLE 2

Percentage of mucoadhesion of the product - Example solid composition 4, diluted 1:2.5 and 1:5 towards human buccal cells.

| Samples | Diluted 1:2.5 | Diluted 1:5 |
|---|---|---|
| A | 63.8 | 48.5 |
| B | 57.7 | 40.6 |
| C | 66.4 | 52.3 |
| Mean ± S.D. | 62.6 ± 4.5 | 47.1 ± 3.5 |

Dilution 1:2.5 versus 1:5 $p < 0.01$

TABLE 3

Percentage of mucoadhesion of the product - Example fluid composition 4, undiluted or diluted (1:2 and 1:5) towards human buccal cells.

| Samples | Undiluted | Diluted 1:2 | Diluted 1:5 |
|---|---|---|---|
| A | 74.7 | 64.2 | 58.3 |
| B | 82.4 | 73.4 | 56.6 |
| C | 71.8 | 48.8 | 51.5 |
| Mean ± S.D. | 76.3 ± 5.4 | 66.4 ± 6.1 | 54.6 ± 5.1 |

Undiluted versus Diluted 1:2 $p > 0.05$.
Undiluted vs 1:5 $p < 0.05$;
Diluted 1:2 versus Diluted 1:5 $p > 0.05$

TABLE 4

Percentage of mucoadhesion of the product - Example fluid composition 3, undiluted or diluted (1:2 and 1:5) towards human buccal cells.

| Samples | Undiluted | Diluted 1:2 | Diluted 1:5 |
|---|---|---|---|
| A | 75.6 | 61.6 | 53.6 |
| B | 73.8 | 64.8 | 49.7 |
| C | 70.3 | 58.7 | 51.5 |
| Mean ± S.D. | 73.2 ± 2.7 | 61.7 ± 3.1 | 51.6 ± 2.0 |

Undiluted versus Diluted 1:2 $p < 0.01$;
Diluted 1:2 versus Diluted 1:5 $p < 0.01$ In the second phase of the experimentation, the composition ability to remain adhered to the mucous membrane over time was assessed, by subjecting the system to a 2 ml/min flow of artificial saliva, made of an isotonic aqueous solution containing a pH 7 phosphate buffer and 0.5% mucin. The results obtained highlighted an interesting product ability to remain bioadhered to mucous membranes during the first hour of application.

The resistance of the mucoadhesive layer obtained with the composition Example solid composition 3, diluted 1:2.5 at different times, 0.5 h 1 h and 2 h towards a simulated salivary solution (0.9% NaCl physiological solution) is reported in Table 5, below.

| Samples | 0 Hours | 0.5 Hours | 1 Hour | 2 Hours |
|---|---|---|---|---|
| A | 69.5 | 63.4 | 54.7 | 43.3 |
| B | 71.4 | 55.8 | 48.8 | 34.8 |
| C | 65.6 | 52.3 | 47.5 | 40.2 |
| Mean ± S.D. (%) | 68.8 ± 3.0 | 57.2 ± 5.6 | 50.3 ± 3.8 | 39.4 ± 4.3 |

Time 0 hours versus Time 0.5 hours $p < 0.05$;
Time 0.5 hours versus Time 1 hour $p > 0.05$
Time 2 hours versus Time 1 hour $p < 0.05$

TABLE 6 resistance of the mucoadhesive layer obtained with the composition Children Tablets Formula 150728/1, diluted 1:2.5 at different times, 0.5 h 1 h and 2 h, towards a simulated salivary solution (0.9% NaCl physiological solution).

| Samples | 0 Hours | 0.5 Hours | 1 Hour | 2 Hours |
|---|---|---|---|---|
| A | 63.8 | 58.5 | 52.3 | 35.5 |
| B | 57.7 | 52.8 | 47.9 | 31.6 |
| C | 66.4 | 62.2 | 53.5 | 38.2 |
| Mean ± S.D. | 62.6 ± 4.5 | 57.8 ± 4.7 | 51.2 ± 2.9 | 35.1 ± 3.3 |

Time 0 hours versus Time 0.5 hours $p > 0.05$;
Time 0.5 hours versus Time 1 hour $p < 0.05$
Time 2 hours versus Time 1 hour $p < 0.01$

TABLE 7

Resistance of the mucoadhesive layer obtained with the composition - Example fluid composition 4, diluted 1:2 at different times (0.5-2 h) towards an artificial salivary solution.

| Samples | 0 Hours | 0.5 Hours | 1 Hour | 2 Hours |
|---|---|---|---|---|
| A | 64.2 | 63.5 | 55.6 | 47.2 |
| B | 73.3 | 68.9 | 52.8 | 43.7 |
| C | 61.7 | 58.4 | 46.3 | 38.5 |
| Mean ± S.D. | 66.4 ± 6.1 | 63.6 ± 5.3 | 51.6 ± 4.8 | 43.1 ± 4.4 |

Time 0 hours versus Time 0.5 hours $p > 0.05$;
Time 0.5 hours versus Time 1 hour $p < 0.05$
Time 1 hour versus Time 0 hours $p < 0.01$;
Time 2 hours versus Time 1 hour $p > 0.05$

TABLE 8

Resistance of the mucoadhesive layer obtained with the product Example fluid composition 3, diluted 1:2 at different times (0.5-2 h) towards an artificial salivary solution.

| Samples | 0 Hours | 0.5 Hours | 1 Hour | 2 Hours |
|---|---|---|---|---|
| A | 61.6 | 55.3 | 50.5 | 45.2 |
| B | 64.8 | 51.8 | 48.3 | 40.6 |
| C | 58.7 | 47.4 | 41.6 | 38.5 |
| Mean ± S.D. | 61.7 ± 3.1 | 51.5 ± 4.0 | 46.8 ± 4.7 | 41.4 ± 3.4 |

Time 0 hours versus Time 0.5 hours $p < 0.05$;
Time 0.5 hours versus Time 1 hour $p > 0.05$
Time 1 hour versus Time 0 hours $p = 0.01$;
Time 2 hours versus Time 1 hour $p > 0.05$ The results obtained in this experimentation demonstrate that the different formulations of the composition of the invention possess a high mucoadhesive ability towards buccal cells. Moreover, the assessment of the resistance of the mucoadhesive-protective layer to flow with an artificial salivary solution allowed to highlight a good mucoadhesion retentive ability during the first hour of application.

In light of the results obtained, it is possible to state that the composition of the invention, demonstrating to possess good, resistant mucoadhesivity, can play a real protective role on oropharyngeal mucous membrane.

2. Barrier Assay

Object of the assay is to demonstrate the action mechanism of the composition of the invention, by assaying its filmogenic and protective ability compared to a known irritating agent: the agent used is lipopolysaccharide (LPS) membrane, a classic model of inflammatory induction. Said assay aims at highlighting the effective ability of the product to limit contact between the mucous membrane and external irritating agents.

The selected irritating agent was isolated from *Escherichia coli* cell membrane. LPS dimensions are such as to allow to consider the barrier effective in protecting the mucous membrane from dust, smog, pollens and other agents concurring to irritation, and therefore to the onset of different pathologies burdening this particular and delicate environment.

Analyzing the experimental protocol in more detail, the sample ability to act as barrier is assessed by measuring IL6 production and which consequence of the contact between a layer of cells (fibroblasts) and the LPS. The experimental system provides the use of special Transwell wells, equipped with a collagen-coated semipermeable membrane that prevents direct contact between cells, deposited on the bottom, and sample, stratified on the overhanging semipermeable membrane, which represents the sole communication route between the 2 portions of the well. LPS is inoculated in the space above the sample, whereby membrane crossing will be all the more difficult the greater the barrier effect exerted by the sample itself. Therefore, the quantification of interleukins produced at +24 hours from LPS addition yields a direct evidence of the barrier effect exerted by the assayed sample. IL6 inhibition is a direct measurement of the barrier effect.

The barrier effect (BE) is expressed as a percentage of the reduction of the release of IL-6 and is obtained through comparison with the value obtained from the Positive Do Control (C+), i.e. from cells treated with the sole LPS in the absence of the sample.

% BE=% inhibition of IL-6 (pg/ml) produced

The results obtained in the experiment conducted in triplicate with different embodiments of the composition of the invention are reported in the following tables. Due to the presence of resins in high concentrations, the barrier assay was carried out both on the 1:2.5 diluted product and on the 1:5 diluted product. First the cell-secreted IL6 picograms after LPS insult, and, in the next Table, the % inhibition compared to the positive control are reported.

TABLE 9

IL6 production in barrier assay with a formulation of the composition of the invention in adult tablets (Example solid composition 3) according to the examples reported in the detailed section of the invention.

| | Sample | IL-6 (pg/μL) | Mean | Std Dev. |
|---|---|---|---|---|
| Adult Tablets | 1:5 + LPS 1 | 330.41 | 343.814 | 13.77 |
| | 1:5 + LPS 2 | 357.924 | | |
| | 1:5 + LPS 3 | 343.109 | | |
| | 1:2.5 + LPS 1 | 314.184 | 329.234 | 13.336 |
| | 1:2.5 + LPS 2 | 339.581 | | |
| | 1:2.5 + LPS 3 | 333.938 | | |
| | 1:5 + LPS 1 | 281.027 | 308.54 | 24.752 |
| | 1:5 + LPS 1 | 328.999 | | |
| | 1:5 + LPS 1 | 315.595 | | |
| | 1:2.5 + LPS 1 | 326.883 | 350.399 | 20.378 |
| | 1:2.5 + LPS 2 | 362.662 | | |
| | 1:2.5 + LPS 3 | 361.451 | | |

TABLE 9-continued

IL6 production in barrier assay with a formulation of the composition of the invention in adult tablets (Example solid composition 3) according to the examples reported in the detailed section of the invention.

| Sample | IL-6 (pg/μL) | Mean | Std Dev. |
|---|---|---|---|
| Control + 1 (LPS) | 638.705 | 675.86 | 32.554 |
| Control + 2 (LPS) | 689.499 | | |
| Control + 3 (LPS) | 699.376 | | |
| Control − 1 (MEM) | 62.328 | 64.679 | 3.48 |
| Control − 2 (MEM) | 63.033 | | |
| Control − 3 (MEM) | 68.677 | | |

From the results, a remarkable reduction of the concentration of IL-6 produced in the experiments in which the assayed product is present is evident, at both dilutions, exhibiting a barrier protracted in time, effective also in case of partial loss of product due to inability to slowly dissolve the tablet in the mouth.

The IL-6 value equal to 64.6 pg/μL, detected for the negative control, is assimilable to a normal basal value, i.e. to a non-inflammatory condition. The graph in FIG. 2A clearly shows the protection exerted by the product on the cells: the data are expressed in terms of fold over (F. O.) compared to the control C−.

From the mean IL-6 values measured in the barrier assay and in the positive control, the percentage of IL-6 release reduction is calculated:

$$100-[(\text{IL-6SAMPLE})/\text{IL-6C+})\times 100]$$

Therefore, by applying the formula it is obtained a value of reduction of IL-6 production, in the presence of the assayed sample, which is of 54% at 1:5 dilutions and of 48% at 1:2.5 dilutions, compared to the positive control reported in Table 10 for the composition of the invention made in the form of adult tablets (Example solid composition 3) as described in the detailed section above

| | | Barrier Effect | | |
|---|---|---|---|---|
| | Sample | IL6 Release inhibition % | Mean | Std Dev. |
| Adults tablets | 1:5 + LPS 1 | 58.419 | 54.348 | 3.662 |
| | 1:5 + LPS 2 | 51.321 | | |
| | 1:5 + LPS 3 | 53.305 | | |
| | 1:2.5 + LPS 1 | 51.635 | 43.155 | 3.015 |
| | 1:2.5 + LPS 2 | 46.311 | | |
| | 1:2.5 + LPS 3 | 46.52 | | |
| CONTROL + 1 (LPS) | | 0 | 0 | 0 |
| CONTROL + 2 (LPS) | | 0 | | |
| CONTROL + 3 (LPS) | | 0 | | |

TABLE 11

IL6 production in barrier assay with a formulation of the composition of the invention in children tablets (example solid composition 4) according to the examples reported in the detailed section of the invention.

| | Sample | IL-6 (pg/μL) | Mean | Std Dev. |
|---|---|---|---|---|
| children Tablets | 1:5 + LPS 1 | 330.41 | 343.814 | 13.77 |
| | 1:5 + LPS 2 | 357.924 | | |
| | 1:5 + LPS 3 | 343.109 | | |
| | 1:2.5 + LPS 1 | 314.184 | 329.234 | 13.336 |
| | 1:2.5 + LPS 2 | 339.581 | | |
| | 1:2.5 + LPS 3 | 333.938 | | |

TABLE 11-continued

IL6 production in barrier assay with a formulation of
the composition of the invention in children tablets (example
solid composition 4) according to the examples reported
in the detailed section of the invention.

| Sample | IL-6 (pg/µL) | Mean | Std Dev. |
|---|---|---|---|
| Control + 1 (LPS) | 638.705 | 675.86 | 32.554 |
| Control + 2 (LPS) | 689.499 | | |
| Control + 3 (LPS) | 699.376 | | |
| Control − 1 (MEM) | 62.328 | 64.679 | 3.48 |
| Control − 2 (MEM) | 63.033 | | |
| Control − 3 (MEM) | 68.677 | | |

From the mean IL-6 values measured in the barrier assay and in the positive control, the percentage of IL-6 release reduction is calculated: 100−[(IL-SAMPLE)/IL-6C+)×100]

Therefore, by applying the formula it is obtained a value of reduction of IL-6 production, in the presence of the assayed sample, which is of 49% at 1:5 dilutions and of 51% at 1:2.5 dilutions, compared to the positive control reported in Table 12 for the composition of the invention made in the form of children tablets (Example solid composition 4) as described in the detailed section above.

Barrier Effect

| Sample | | IL6 Release inhibition % | Mean | Std Dev. |
|---|---|---|---|---|
| Children Tablets | 1:5 + LPS 1 | 51.113 | 49.129 | 2.037 |
| | 1:5 + LPS 2 | 47.042 | | |
| | 1:5 + LPS 3 | 49.234 | | |
| | 1:2.5 + LPS 1 | 53.513 | 51.287 | 1.973 |
| | 1:2.5 + LPS 2 | 49.756 | | |
| | 1:2.5 + LPS 3 | 50.591 | | |
| CONTROL + 1 (LPS) | | 0 | 0 | 0 |
| CONTROL + 2 (LPS) | | 0 | | |
| CONTROL + 3 (LPS) | | 0 | | |

Values rounded off to 3 decimal digits

TABLE 13

IL6 production in the barrier assay with formulation
of the composition of the invention in strong spray (Example
fluid composition 3) according to the examples reported
in the detailed section of the invention.

| Sample | IL-6 (pg/µl) | Mean | DS |
|---|---|---|---|
| STRONG SPRAY + LPS 1 | 392.915 | 413.188 | 22.109 |
| STRONG SPRAY + LPS 2 | 409.88 | | |
| STRONG SPRAY + LPS 3 | 436.761 | | |
| CONTROL + 1 (LPS) | 639.728 | 676.973 | 32.634 |
| CONTROL + 2 (LPS) | 690.646 | | |
| CONTROL + 3 (LPS) | 700.547 | | |
| CONTROL − 1 (MEM) | 61.945 | 64.303 | 3.489 |
| CONTROL − 2 (MEM) | 62.662 | | |
| CONTROL − 3 (MEM) | 68.310 | | |

From the mean IL-6 values measured in the barrier assay and in the positive control, the percentage of IL-6 release reduction is calculated: 100−[(IL-SAMPLE)/IL-6C+)×100]

Therefore, by applying the formula it is obtained a value of reduction of IL-6 production, in the presence of the assayed sample, which is of 39% compared to the positive control reported in Table 14 for the composition of the invention made in the form of strong spray (Example fluid composition 3) as described in the detailed section above.

| SAMPLE | IL6 Release inhibition % | MEAN | D.S |
|---|---|---|---|
| STRONG SPRAY + LPS 1 | 41.960 | 38.965 | 3.266 |
| STRONG SPRAY + LPS 2 | 39.453 | | |
| STRONG SPRAY + LPS 3 | 35.483 | | |

Table 15 below, IL6 production in the barrier assay with formulation of the composition of the invention in no alcohol spray (Example fluid composition 4) according to the examples reported in the detailed section of the invention.

| SAMPLE | IL-6 (pg/µl) | MEAN | DS |
|---|---|---|---|
| NO ALCOHOL SPRAY + LPS 1 | 285.128 | 297.914 | 11.054 |
| NO ALCOHOL SPRAY + LPS 2 | 308.051 | | |
| NO ALCOHOL SPRAY + LPS 3 | 299.554 | | |
| CONTROL + 1 (LPS) | 639.728 | 676.973 | 32.634 |
| CONTROL + 2 (LPS) | 690.646 | | |
| CONTROL + 3 (LPS) | 700.547 | | |
| CONTROL − 1 (MEM) | 61.945 | 64.303 | 3.489 |
| CONTROL − 2 (MEM) | 62.662 | | |
| CONTROL − 3 (MEM) | 68.310 | | |

From the mean IL-6 values measured in the barrier assay and in the positive control, the percentage of IL-6 release reduction is calculated: 100−[(IL-6 SAMPLE)/IL-6C+)×100]

Therefore, by applying the formula it is obtained a value of reduction of IL-6 production, in the presence of the assayed sample, which is of 56% compared to the positive control reported in Table 16 for the composition of the invention made in the form of no alcohol spray (Example fluid composition 4) as described in the detailed section above.

| Sample | IL6 Release inhibition % | MEAN | D.S. |
|---|---|---|---|
| NO ALCOHOL SPRAY + LPS1 | 57.734 | 55.993 | 1.633 |
| NO ALCOHOL SPRAY + LPS2 | 54.496 | | |
| NO ALCOHOL SPRAY + LPS3 | 55.749 | | |

To validate the method used, and to verify that the results depend on the sole barrier effect of the assayed samples and exclude any pharmacological, immunological or metabolic effects (e.g., cytokine synthesis modulation), the barrier assay was assisted by an INTERNAL CONTROL (IC) concomitantly carried out on each sample.

In the IC assay, first the cells are stimulated with the LPS, whereas the sample is added to the Transwell only subsequently: in this case, a nil % of IL6 inhibition would clearly indicate that the presence of the assayed composition affords a mechanical protection, in no way interfering with cellular cytokine synthesis.

IL-6 concentration values measured in internal control experiments, wherein said treatment with the composition in the form of adult tablets (Example solid composition 3) is carried out after LPS insult, are reported in Table 17 below:

| Fold over compared to C− in the Internal Control | | | | |
|---|---|---|---|---|
| SAMPLE | | F.O. (C−) | Mean (%) | Std Dev. (%) |
| Adults Tablets | 1:5 + LPS 1 | 11.821 | 12.059 | 0.229 |
| | 1:5 + LPS 2 | 12.278 | | |
| | 1:5 + LPS 3 | 12.076 | | |
| | 1:2.5 + LPS 1 | 10.97 | 11.112 | 0.185 |
| | 1:2.5 + LPS 2 | 11.321 | | |
| | 1:2.5 + LPS 3 | 11.045 | | |
| CONTROL + 1 (LPS) | | 13.767 | 12.427 | 1.207 |
| CONTROL + 2 (LPS) | | 12.087 | | |
| CONTROL + 3 (LPS) | | 11.427 | | |
| CONTROL − 1 (MEM) | | 1.099 | 1 | 0.096 |
| CONTROL − 2 (MEM) | | 0.908 | | |
| CONTROL − 3 (MEM) | | 0.993 | | |

Values rounded off to 3 decimal digits

IL-6 concentration values measured in internal control experiments, wherein said treatment with the composition in the form of children tablets (Example solid composition 4) is carried out after LPS insult, are reported in Table 18 below:

| Fold over compared to C− in the Internal Control | | | | |
|---|---|---|---|---|
| SAMPLE | | F.O. (C−) | Mean (%) | Std Dev. (%) |
| Children Tablets | +LPS 1 | 11.172 | 10.002 | 1.015 |
| | +LPS 2 | 9.481 | | |
| | +LPS 3 | 9.353 | | |
| | .5 + LPS 1 | 11.598 | 11.903 | 0.339 |
| | .5 + LPS 2 | 12.268 | | |
| | .5 + LPS 3 | 11.842 | | |
| CONTROL + 1 (LPS) | | 13.767 | 12.427 | 1.207 |
| CONTROL + 2 (LPS) | | 12.087 | | |
| CONTROL + 3 (LPS) | | 11.427 | | |
| CONTROL − 1 (MEM) | | 1.099 | 1 | 0.096 |
| CONTROL − 2 (MEM) | | 0.908 | | |
| CONTROL − 3 (MEM) | | 0.993 | | |

Values rounded off to 3 decimal digits

IL-6 concentration values measured in internal control experiments, wherein said treatment with the composition in the form of strong spray (Example solid composition 3) is carried out after LPS insult, are reported in Table 19 below:

| SAMPLE | IL-6 (pg/μl) | MEAN | D.S |
|---|---|---|---|
| STRONG SPRAY + LPS 1 | 839.865 | 839.158 | 4.637 |
| STRONG SPRAY + LPS 2 | 843.401 | | |
| STRONG SPRAY + LPS 3 | 834.208 | | |
| CONTROL + 1 (LPS) | 914.828 | 825.721 | 80.223 |
| CONTROL + 2 (LPS) | 803.091 | | |
| CONTROL + 3 (LPS) | 759.244 | | |
| CONTROL − 1 (MEM) | 72.553 | 65.953 | 6.378 |
| CONTROL − 2 (MEM) | 59.824 | | |
| CONTROL − 3 (MEM) | 65.481 | | |

IL-6 concentration values measured in internal control experiments, wherein said treatment with the composition in the form of no alcohol spray (Example fluid composition 4) is carried out after LPS insult, are reported in Table 20 below:

| SAMPLE | IL-6 (pg/μl) | MEAN | D.S |
|---|---|---|---|
| NO ALCOHOL SPRAY + LPS 1 | 759.244 | 744.157 | 22.557 |
| NO ALCOHOL SPRAY + LPS 2 | 755.001 | | |
| NO ALCOHOL SPRAY + LPS 3 | 718.227 | | |
| CONTROL + 1 (LPS) | 914.828 | 825.721 | 80.223 |
| CONTROL + 2 (LPS) | 803.091 | | |
| CONTROL + 3 (LPS) | 759.244 | | |
| CONTROL − 1 (MEM) | 72.553 | 65.953 | 6.378 |
| CONTROL − 2 (MEM) | 59.824 | | |
| CONTROL − 3 (MEM) | 65.481 | | |

The values obtained in these experiments are found to be homogeneous with those of the positive control for the barrier assay (sample absence), and confirm how the sample applied after LPS insult does not influence the production of inflammation mediators, and therefore has no direct anti-inflammatory effect. This is better represented in the graphs reported in FIG. 5, expressing the values of cell-produced IL-6 in terms of Fold Over C.

3. DPPH Assay for Radical-Scavenger Activity

The scavenger anti-oxidising activity directed by the extract of poplar buds according to the present description (obtained with the above-described method and having the above-described characteristics) was assessed by DPPH (2,2-diphenyl-1-picrylhydrazyl) assay; DPPH is a coloured stable radical: it changes colour when chemically reacting with an anti-oxidising compound, and can be detected by spectrophotometric reading. Therefore, object of this assay is to demonstrate that the analysed samples possess a good anti-oxidising activity which is carried out in a purely chemical way (hydrogen transfer to a free radical) without involving pharmacological, immunological or metabolic mechanisms when applied on biological substrates. The analysed sample is the extract of poplar buds according to the present description, at 1000, 100 and 10 μg/mL concentrations. The activity was compared to that of vitamin C, used as positive control.

As is visible from FIG. 6, the extract of poplar buds according to the invention exhibits excellent anti-oxidising activity at the higher concentrations of 1000 and 100 μg/ml and good activity at the lower concentration of 10 μg/ml.

4. Biofilm Formation Inhibition Assay

The methodology used in this assay exploits microorganism ability to adhere and form biofilms on polystyrene plate wells: the biofilm mass will then be determined by Crystal-violet staining. The bacterium used in the assay is the one most frequently involving infections of the pharyngeal mucous membrane, i.e., *Streptococcus pyogenes*; the analysed sample is the extract of poplar buds according to the present description (obtainable with the above-described method and having the above-described characteristics). The first phase of the assay consists in the assessment of the minimum inhibitory concentration (MIC), i.e., the lowest sample concentration inhibiting microorganism growth. The antibiotic gentamycin was selected as positive control. In the second phase, the ability to inhibit biofilm formation is measured; the assayed samples are added to the medium in concentrations equal to or lower than the MIC, to rule out that the antibiofilm activity be ascribable to a microbial growth inhibition. After an adequate incubation period, the biofilm formed was stained with Crystal-violet; following staining, excess dye was removed with water, and that adhered to biofilm was dissolved in ethanol. The resulting solution was analysed by spectrophotometer at 570 nm: the intensity of absorbance from this analysis will be all the greater the greater the mass of biofilm formed; accordingly, anti-biofilm activity and recorded absorbance are inversely proportional to each other. For each sample, the concentrations used were 1×MIC, 0.5×MIC and 0.1 MIC. The reported data are the mean of 9 measurements carried out in triplicate. Statistical significance calculated with the t test, *p<0.01 and **p<0.001 (treated bacteria versus untreated bacteria). The assay shows how the extract of the invention is more effective compared to a standard 50% hydro-alcoholic extract.

5. Comparative Assay of Mucoadhesion and Resistance to Washing Between Composition According to the Invention, in Different Embodiments Thereof, and Propolis Spray Propolis Spray

| | |
|---|---|
| deionised water in | %33 |
| propolis d.e. multi-f. | %41.6 |
| plant glycerine a | %55 |
| lemon loose E.O. | %0.1 |

No Alcohol Propolis Spray

| | |
|---|---|
| deionised water in | %57.2 |
| propolis, lyoph. extract e | %4 |
| CHERRY FLAVOUR nat. p | %0.8 |
| strawberry natural flavour | %1.2 |
| clear lemon juice | %1.8 |
| plant glycerine a | %35 |

The assays were carried out as described above for example 1, assaying the compositions of the invention and a propolis spray at different dilutions.

The data reported in the tables show how, above all at higher dilutions, the compositions of the invention have greater mucoadhesive effect compared to propolis.

TABLE 21

| | | Propolis spray |
|---|---|---|
| MUCOADHESION | Diluted 1:2: 68.8 ± 3.0 | Undiluted: |
| | Diluted 1:5: 55.6 ± 1.8 | Diluted 1:2: 57.5 ± 3.1 |
| | | Diluted 1:5: 36.8 ± 5.0 |
| Resistance to washing | Diluted 1:2: 68.8 ± 3.0 | Diluted 1:2: 57.5 ± 3.1 |
| | 30 min: 57.2 ± 5.6 | 30 min: 54.4 ± 2.1 |
| | 60 min: 50.3 ± 3.8 | 60 min 52.5 ± 2.7 |
| | 120 min: 39.4 ± 4.3 | 120 min: 34.1 ± 1.6 |

TABLE 22

| | Children Tablets | Propolis spray |
|---|---|---|
| MUCOADHESION | Diluted 1:2: 62.6 ± 4.5 | Undiluted |
| | Diluted 1:5: 47.1 ± 3.5 | Diluted 1:2: 57.5 ± 3.1 |
| | | Diluted 1:5: 36.8 ± 5.0 |
| Resistance to washing | Diluted 1:2: 62.6 ± 4.5 | Diluted 1:2: 57.5 ± 3.1 |
| | 30 min: 57.8 ± 4.7 | 30 min: 54.4 ± 2.1 |
| | 60 min: 51.2 ± 2.9 | 60 min 52.5 ± 2.7 |
| | 120 min: 35.1 ± 3.3 | 120 min: 34.1 ± 1.6 |

TABLE 23

| | STRONG SPRAY | Propolis spray |
|---|---|---|
| MUCOADHESION | Undiluted 76.3 ± 5.4 | Undiluted |
| | Diluted 1:2: 66.4 ± 6.1 | Diluted 1:2: 57.5 ± 3.1 |
| | Diluted 1:5: 54.6 ± 5.1 | Diluted 1:5: 36.8 ± 5.0 |

TABLE 23-continued

| | STRONG SPRAY | Propolis spray |
|---|---|---|
| Resistance to washing | Diluted 1:2 66.4 ± 6.1 | Diluted 1:2: 57.5 ± 3.1 |
| | 30 min: 63.6 ± 5.3 | 30 min: 54.4 ± 2.1 |
| | 60 min 51.6 ± 4.8 | 60 min 52.5 ± 2.7 |
| | 120 min: 43.1 ± 4.4 | 120 min: 34.1 ± 1.6 |

TABLE 24

| | No alcohol spray | Propolis spray |
|---|---|---|
| Mucoadhesion | Undiluted: 73.2 ± 2.7 | Undiluted |
| | Diluted1:2: 61.7 ± 3.1 | Diluted1:2: 57.5 ± 3.1 |
| | Diluted1:5: 51.6 ± 2.0 | Diluted1:5: 36.8 ± 5.0 |
| resistance to washing | Diluted1:2: 61.7 ± 3.1 | Diluted1:2: 57.5 ± 3.1 |
| | 30 min: 51.5 ± 4.0 | 30 min: 54.4 ± 2.1 |
| | 60 min 46.8 ± 4.7 | 60 min 52.5 ± 2.7 |
| | 120 min: 41.4 ± 3.4 | 120 min: 34.1 ± 1.6 |

As is apparent from the above-reported assays, the assayed compositions show how, in any embodiment assayed (solid, spray with alcohol, spray without alcohol), the extract of poplar buds possesses a mucoadhesive ability greater than that of propolis, appreciable in particular at higher dilutions of the assayed products, as evident from data obtained with 1:5 dilutions.

6. Preparation of the Hydro-Alcoholic Multi-Fraction Extract

Black poplar (*Populus nigra*) buds were fragmented and subjected to two extraction steps, by extractor equipped with mechanical stirrer, in ethanol at decreasing concentrations, performing the first step with 85% ethanol and a second step with 13% ethanol. The D/S ratio used is equal to 1:6. The extraction temperature is equal to 40° C. The extraction length with 85° ethanol is equal to 8 hours, the extraction length with 13° ethanol is equal to 8 hours.

The alcoholic extracts obtained as described were reunited in a 50:50 ratio. Mixing envisaged adding the 13° alcoholic extract into the 85° alcoholic extract (with an addition rate equal to 16 l/min). The mixing was carried out at 20°±5° C. At the end of the addition the mixture was subjected to decantation for 72 hours at 20°±5° C., then the supernatant was recovered and further filtered on a panel filter equipped with a cellulose filter with a 30 μm cut-off. At the end of the filtering, alcohol gradation is checked and adjusted to 62°±1° alcohol grades.

7. Preparation of the Lyophilised Multi-Fraction Extract

The clarified alcoholic extract obtained as described in Example 1, with no correction to the alcohol gradation, is concentrated by ethanol evaporation, by use of a thin film distillation system according to a standard protocol, envisaging the feeding of the extract to be concentrated at a flow rate of about 500 l/h; the operation is carried out by setting a residual vacuum of 0.6-0.8 bar, and the fluid heating the evaporation walls is set at 140° C., thereby obtaining, after ethanol elimination, a concentrated aqueous extract. The aqueous extract thus obtained was subjected to lyophilisation.

8. Preparation of the Lyophilised Multi-Fraction Extract Supported on Arabic Gum The clarified alcoholic extract obtained as described in Example 1 is mixed with Arabic gum and subjected to concentration and lyophilisation as described in Example 2.

The invention claimed is:
1. A method of treating an oropharyngeal cavity condition in a person in need thereof, comprising administering an effective amount of a composition comprising an extract of poplar buds to a percentage in weight from about 0.1 to about 70% and one or more pharmaceutically acceptable carrier, excipient, flavor, and preservative; wherein said extract of poplar buds is obtained by:
- (a) preparing a hydro-alcoholic extract of poplar buds by extraction with 85% ethanol;
- (b) preparing a hydro-alcoholic extract of poplar buds by extraction with 13% ethanol;
- (c) obtaining a multi-fraction alcoholic extract, by mixing the extracts prepared in (a) and (b);
- (d) decanting and/or centrifuging and filtering said alcoholic extract (c) collecting the supernatant; and
- (e) subjecting the filtered supernatant obtained in (d) to concentration and freeze-drying.

2. The method according to claim 1, wherein said composition comprises an extract of poplar buds at a percentage in weight from about 0.3 to about 45%.

3. The method of claim 1, wherein the oropharyngeal cavity condition is selected from sore throat, pharyngitis, aphtha, oral cavity inflammation or infection.

4. The method of claim 1, wherein the composition is a solution, and wherein the composition is selected from:
- (i) poplar bud extract at a percentage in weight of about 0.7%, xantham gum at a percentage in weight of about 1%, water at a percentage in weight of about 55.40%, peach flavor at a percentage in weight of about 0.4%, lemon flavor at a percentage in weight of about 0.1%, clear lemon juice at a percentage in weight of about 1.4%, edible plant glycerine at a percentage in weight of about 15%, orange juice at a percentage in weight of about 26%;
- (ii) poplar bud extract at a percentage in weight of about 1.0%, guar gum at a percentage in weight of about 1%, water at a percentage in weight of about 55.10%, peach flavor at a percentage in weight of about 0.4%, lemon flavor at a percentage in weight of about 0.1%, clear lemon juice at a percentage in weight of about 1.4%, edible plant glycerine at a percentage in weight of about 15%, orange juice at a percentage in weight of about 26%;
- (iii) poplar bud extract at a percentage in weight of about 0.55%, Arabic gum at a percentage in weight of about 4.95%, water at a percentage in weight of about 51.30%, cherry flavor at a percentage in weight of about 0.2%, strawberry flavor at a percentage in weight of about 0.6%, clear lemon juice at a percentage in weight of about 1.4%, edible plant glycerine at a percentage in weight of about 35%, clear apple juice concentrate 70×BIS at a percentage in weight of about 6%; and
- (iv) alcoholic poplar bud extract 62° at a percentage in weight of about 39.76%, deionized water at a percentage in weight of about 3.92%, plant glycerine at a percentage by weight of about 55.70%, lemon loose essential oil at a percentage in weight of about 0.01%, sweet orange loose essential oil at a percentage in weight of about 0.01%, citrus natural flavor at a percentage in weight of about 0.6%.

5. The method of claim 1, wherein the composition is a solid, and wherein the composition is selected from:
- (i) lyophilized poplar buds extract at a percentage in weight of about 5.0%, mannitol at a percentage in weight of about 46.14%, tara gum at a percentage in weight of about 6.56%, inulin at a percentage in weight of about 38.60%, raspberry lyophilized juice at a percentage in weight of about 0.40%, peach lyophilized juice at a percentage in weight of about 2.50%, lemon natural flavor at a percentage in weight of about 0.80%, cherry natural flavor at a percentage in weight of about 1%, mallow lyophilized extract at a percentage in weight of about 0.8%;
- (ii) lyophilized poplar buds extract at a percentage in weight of about 10.0%, sorbitol at a percentage in weight of about 46.14%, guar gum at a percentage in weight of about 1.56%, inulin at a percentage in weight of about 15%, lemon lyophilized juice at a percentage in weight of about 0.40%, orange lyophilized juice at a percentage in weight of about 25%, lemon natural flavor at a percentage in weight of about 0.80%, raspberry natural flavor at a percentage in weight of about 1.10%, mallow lyophilized extract at a percentage in weight of about 0.8%;
- (iii) lyophilized poplar buds extract at a percentage in weight of about 1.08%, brown sugar at a percentage in weight of about 71.5%, Arabic gum at a percentage in weight of about 10.82%, honey at a percentage in weight of about 3%, lime (tree) extract at a percentage in weight of about 1.5%, orange lyophilized juice at a percentage in weight of about 10.5%, orange flavor at a percentage in weight of about 1.5%, lemon essential oil at a percentage in weight of about 0.1%; and
- (iv) lyophilized poplar buds extract at a percentage in weight of about 1.14%, brown sugar at a percentage in weight of about 83.5%, Arabic gum at a percentage in weight of about 6.56%, inulin at a percentage in weight of about 1.6%, strawberry lyophilized juice at a percentage in weight of about 2.40%, elder lyophilized juice at a percentage in weight of about 2.0%, strawberry natural flavor at a percentage in weight of about 1.0%, cherry natural flavor at a percentage in weight of about 1%, Lime (tree) lyophilized extract at a percentage in weight of about 0.8%.

6. The method according to claim 1, wherein the composition comprises:
Poplar buds extract at a percentage in weight from 0.1 to 70%,
Excipients at a percentage in weight from 1 to 80%,
Natural or artificial flavours at a percentage in weight from 0.05 to 2%, and
Essential oils at a percentage in weight from 0.01 to 1%.

7. The method according to claim 1, wherein the composition comprises:
Dry poplar buds extract at a percentage in weight from 0.5 to 10%,
Excipients at a percentage in weight of 10-97%,
Natural or artificial flavours at a percentage in weight from 0.5 to 3%,
Essential oils at a percentage in weight from 0.05 to 1%,
Powdered or lyophilised fruit juices and/or natural extracts at a percentage in weight from 0.5 to 15%, and
Sweeteners at a percentage in weight from 1 to 10%.

8. The method according to claim 6, wherein the composition further comprises:
Solvents at a percentage in weight less than or equal to 80%,
Natural or lyophilised fruit juices at a percentage in weight less than or equal to 50%.

* * * * *